United States Patent
Oscanoa Aida et al.

(10) Patent No.: US 12,222,413 B2
(45) Date of Patent: Feb. 11, 2025

(54) RANDOMIZED DIMENSION REDUCTION FOR MAGNETIC RESONANCE IMAGE ITERATIVE RECONSTRUCTION

(71) Applicant: The Board of Trustees of the Leland Stanford Junior University, Stanford, CA (US)

(72) Inventors: Julio A. Oscanoa Aida, Stanford, CA (US); Frank Ong, Palo Alto, CA (US); Mert Pilanci, Palo Alto, CA (US); Shreyas S. Vasanawala, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 279 days.

(21) Appl. No.: 17/744,299

(22) Filed: May 13, 2022

(65) Prior Publication Data
US 2022/0381863 A1    Dec. 1, 2022

Related U.S. Application Data (60) Provisional application No. 63/188,618, filed on May 14, 2021.

(51) Int. Cl.
*G01R 33/561*    (2006.01)
*A61B 5/055*     (2006.01)
(Continued)

(52) U.S. Cl.
CPC .......... *G01R 33/5611* (2013.01); *A61B 5/055* (2013.01); *G01R 33/543* (2013.01); *G06T 11/006* (2013.01)

(58) Field of Classification Search
None
See application file for complete search history.

(56) References Cited

U.S. PATENT DOCUMENTS

| | | | |
|---|---|---|---|
| 7,576,536 B2 * | 8/2009 | Akao | G01R 33/5611 |
| | | | 324/309 |
| 2011/0044524 A1 * | 2/2011 | Wang | G01R 33/5601 |
| | | | 382/131 |

(Continued)

OTHER PUBLICATIONS

Aggarwal, et al. MoDL: Model-based deep learning architecture for inverse problems. 2018. IEEE transactions on medical imaging, 38(2), 394-405.
(Continued)

*Primary Examiner* — Darryl V Dottin
(74) *Attorney, Agent, or Firm* — LUMEN PATENT FIRM (57) ABSTRACT

In a method for magnetic resonance imaging pseudo-randomly undersampled k-space imaging data is acquired with multiple receiver coils of an MRI imaging apparatus. MR image reconstruction is performed to produce a reconstructed MR image from the k-space imaging data by iteratively solving sketched approximations of an original reconstruction problem. The sketched approximations use a sketched model matrix $A_s$ that is a lower-dimensional version of an original model matrix A of the original reconstruction problem. The sketched model matrix $A_s$ preserves the Fourier structure of the MR reconstruction problem and reduces the number of coils actively used during reconstruction.

7 Claims, 4 Drawing Sheets

(51) Int. Cl.
*G01R 33/54* (2006.01)
*G06T 11/00* (2006.01)

(56) References Cited

U.S. PATENT DOCUMENTS

| | | | | |
|---|---|---|---|---|
| 2011/0213700 | A1* | 9/2011 | Sant'Anselmo | G06Q 20/10 235/487 |
| 2013/0221961 | A1* | 8/2013 | Liu | G01R 33/56545 324/307 |
| 2018/0306884 | A1* | 10/2018 | Trzasko | G01R 33/4824 |

OTHER PUBLICATIONS

Hammernik, et al. Learning a variational network for reconstruction of accelerated MRI data. 2018. Magnetic resonance in medicine, 79(6), 3055-3071.

Sandino, et al., Compressed sensing: From research to clinical practice with deep neural networks: Shortening scan times for magnetic resonance imaging. 2020. IEEE signal processing magazine, 37(1), 117-127.

Yang, et al. ADMM-CSNet: A deep learning approach for image compressive sensing. 2018. IEEE transactions on pattern analysis and machine intelligence, 42(3), 521-538.

Huang, et al. A software channel compression technique for faster reconstruction with many channels, Magnetic resonance imaging, 2008, vol. 26, No. 1, pp. 133-141.

Zhang, et al., Coil compression for accelerated imaging with Cartesian sampling. Magnetic resonance in medicine, 2013, 69(2), 571-582.

Oscanoa, et al., S. S. Coil Sketching for fast and memory-efficient iterative reconstruction. Proc. Intl. Soc. Mag. Reson. Med. 29 (2021) ISMRM 28th Annual Meeting, May 15-20, 2021.

Oscanoa et al. Coil-sketched unrolled networks for computationally-efficient deep MRI reconstruction. ISMRM 30th Annual Meeting, London, United Kingdom, May 6-12, 2022.

Pilanci, M., & Wainwright, M. J. (2016). Iterative Hessian sketch: Fast and accurate solution approximation for constrained least-squares. The Journal of Machine Learning Research, 17(1), 1842-1879.

Pilanci, et al., Randomized sketches of convex programs with sharp guarantees.(2015) IEEE Transactions on Information Theory, 61(9), 5096-5115.

Kellman et al., Memory-efficient learning for large-scale computational imaging, 2020. IEEE Transactions on Computational Imaging, vol. 6, pp. 1403-1414.

* cited by examiner

RANDOMIZED DIMENSION REDUCTION FOR MAGNETIC RESONANCE IMAGE ITERATIVE RECONSTRUCTION

CROSS-REFERENCE TO RELATED APPLICATIONS

This application claims priority from U.S. Provisional Patent Application 63/188,618 filed May 14, 2021, which is incorporated herein by reference.

STATEMENT OF FEDERALLY SPONSORED RESEARCH

This invention was made with Government support under contracts EB009690 and EB026136 awarded by the National Institutes of Health, and under contracts 1838179 and 2037304 awarded by the National Science Foundation. The Government has certain rights in the invention.

FIELD OF THE INVENTION

The present invention relates generally to magnetic resonance imaging. More specifically, it relates to techniques for MRI image reconstruction.

BACKGROUND OF THE INVENTION

The combination of parallel imaging and compressed sensing (PICS) is one of the most successful techniques, to date, to accelerate the inherently slow acquisition process of magnetic resonance imaging (MRI). PICS reduces the acquisition time via a pseudorandom undersampling scheme that reduces the amount of data to collect but introduces noise-like artifacts in the images. These artifacts must be later removed using a non-linear iterative reconstruction algorithm. However, the long computation times and large memory requirements of these iterative algorithms remain a bottleneck for clinical deployment, especially in non-Cartesian acquisitions with high dimensionality, i.e. three spatial dimensions plus multiple temporal dimensions, as for example 4D flow, ND flow, dynamic contrast-enhanced imaging, etc.

Furthermore, recently, deep learning (DL) reconstruction frameworks using unrolled network architectures that alternate between denoising and data-consistency have proven to outperform conventional compressed sensing by yielding more accurate and faster reconstructions [1-4]. However, this comes with excessive computational cost, especially for training this CNN-based architectures, as large arrays need to be stored in memory to perform back-propagation. This issue hinders their application to higher dimensional datasets such as dynamic or 3D non-cartesian MRI.

In parallel imaging, the signal is acquired through receiver arrays with multiple coils, where each receiver coil possesses a different spatial sensitivity map and produces a different image that must be stored in memory. Therefore, a general approach to decrease both computation time and memory usage is reducing the number of coils actively used during reconstruction. One class of such methods is coil compression [5,6], which linearly combines multi-coil data into fewer virtual coils prior to reconstruction. While effective for Cartesian imaging, coil compression is inherently less effective for 3D non-Cartesian imaging, due to increased dimensionality and the impossibility to decompose the data into multiple 2D datasets via a preliminary Fourier transform. As a consequence, coil compression usually leads to shading artifacts for non-Cartesian imaging due to energy loss. Another line of work uses the stochastic gradient method, which randomly selects subsets of coil channels for each iteration in reconstruction. While fully leveraging all data, it often requires many iterations for convergence, which extends the already long reconstruction times.

SUMMARY OF THE INVENTION

The present inventors have developed a general and flexible method for computationally-efficient image reconstruction termed "coil sketching"[7,8]. Coil sketching reduces the computational cost by reducing the number of coils actively used during the data consistency step via a randomized sketching approach. The method lowers the computational cost and memory footprint of reconstruction with virtually no penalty on reconstruction accuracy. Furthermore, the method is general enough to be applicable to both conventional and deep learning-based reconstruction methods.

Randomized dimension reduction or randomized sketches techniques [9,10] have been used in other fields of endeavor to enable computations over massive datasets. The basic idea is to project the problem onto a lower-dimensional space, where it can be solved faster and with relatively small memory footprint. However, these dimension reduction techniques are not directly applicable to MRI reconstruction, since a conventional randomized projection would break the Fourier structure of the problem, which would not allow use of the high efficiency of the Fast Fourier Transform. The inventors have discovered how to overcome this problem using a tailored randomized dimension reduction algorithm for MR image reconstruction that synergistically leverages the efficiencies of both the Fourier structure and the randomized formulation, via a carefully designed projection matrix, for enhanced and memory-efficient reconstruction.

In one aspect, the invention provides a method for magnetic resonance imaging comprising: acquiring with multiple receiver coils of an MRI imaging apparatus pseudo-randomly undersampled k-space imaging data; and performing MR image reconstruction to produce a reconstructed MR image from the k-space imaging data. The reconstruction comprises iteratively solving sketched approximations of an original reconstruction problem, wherein the sketched approximations use a sketched model matrix $A_s$ that is a lower-dimensional version of an original model matrix $A$ of the original reconstruction problem. The sketched model matrix $A_s$ preserves the Fourier structure of the MR reconstruction problem and reduces the number of coils actively used during reconstruction. The pseudo-randomly undersampled k-space imaging data may have both spatial and temporal dimensions.

Iteratively solving the sketched approximations of the original reconstruction problem may include iteratively solving second-order Taylor approximations with a sketched Hessian that includes the sketched model matrix $A_S$. The sketched model matrix $A_S$ is preferably related to the original model matrix $A$ by $A^t{}_S = S^t A$, where $S$ is a structured sketching matrix. The structured sketching matrix $S$ is the product of two matrices $S_{PCA}$ and $S_R$, where $S_{PCA}$ estimates virtual coils from principal components and $S_R$ sketches the virtual coils. $S_R$ sketches a reduced number of high-energy virtual coils and also includes random linear combinations of remaining low-energy coils. Multiplication of $S_{PCA}$ by a coil sensitivity map operator C produces a sensitivity map operator $C_{PCA}$ with virtual coils sorted according to descending energy.

DETAILED DESCRIPTION OF THE INVENTION

General Reconstruction

Conventional MR image reconstruction aims to recover image x* by solving the convex optimization problem in Equation 1, $$x^* = \operatorname{argmin}_x f(x) := \underbrace{\frac{1}{2}|Ax - y|_2^2}_{\text{Data Consistency (DC)}} + \underbrace{\lambda R(x)}_{\text{Regularization}} \quad \text{(Eq. 1)}$$

where x represents the image, A models the MR imaging process, y is the acquired undersampled k-space, R is a regularization term, and λ is the regularization hyperparameter. The first term is usually referred as the data consistency term, since it enforces consistency with the acquired data; while the second term is the denoising term that removes the noise-like artifacts based on a prior image representation model. In compressed sensing, the latter term usually denoises by enforcing sparsity in a sparsifying transform domain such as wavelets.

Matrix A has the structure described in Equation 2, $$A = UFC \quad \text{(Eq. 2)}$$

where C represents the voxel-wise multiplication by c coil sensitivity maps, F is the coil-wise Fourier Transform, and U is the undersampling operator. In conventional PICS reconstruction, we would solve Equation 1 using an algorithm like Fast Iterative Shrinkage-Thresholding Algorithm (FISTA) or Alternating Direction Method of Multipliers (ADMM); whereas for DL-based reconstruction the state-of-the-art methods use unrolled networks architectures [1-4]. In all cases, the computational cost of solving Equation 1 is linearly proportional to the number of coils c.

In DL reconstruction with deep unrolled networks, similarly to conventional reconstruction, the reconstruction problem is solved by alternating between data consistency and regularization steps. The difference lies on the regularization step, where the regularization function R(x) is learned from historical data via Convolutional Neural Networks (CNNs). The alternating steps can be described as:

$$x_{k+1} = \mathcal{G}(z_k) \quad \text{(Eq. 3)}$$

$$z_{k+1} = \mathcal{P}_w(x_{k+1}) \quad \text{(Eq. 4)}$$

where $\mathcal{G}$ is the operator enforcing data consistency, $\mathcal{P}$ is enforcing regularization, and k is a step index. In this case, $\mathcal{P}_w$ is composed of CNNs parameterized by W and enforces a learned data-driven regularization. Two common examples of $\mathcal{G}$ operators are shown in equation 5 and equation 6.

$$\mathcal{G}(z) = z - \alpha(A^H(Az - y)) \quad \text{(Eq. 5)}$$

$$\mathcal{G}(z) = \operatorname{argmin}_x |Ax - y|_2^2 + \lambda|x - z|_2^2 \quad \text{(Eq. 6)}$$

where α is the step size.

Sketched Reconstruction

The inventors provide a formulation of the MR reconstruction problem using the iterative Hessian sketching (IHS) formulation [7,8]. Herein, Equation 1 is not directly solved. Instead, the reconstruction is performed by iteratively solving second-order Taylor approximations with a sketched Hessian that includes a lower-dimensional version of the model matrix $A_S^t = S^t A$. The new formulation is presented in Equation 7, where the first term contains the sketched Hessian $(A_S^t)^H A_S^t$ and the second, the gradient $A^H(Ax^t - y)$ of the original problem (without the regularization term).

$$x^{t+1} = \operatorname{argmin}_x \hat{f}(x) := \underbrace{\frac{1}{2}|A_S^t(x - x^t)|_2^2 + \langle x, A^H(Ax^t - y)\rangle}_{\text{Data Consistency (DC)}} + \underbrace{\lambda R(x)}_{\text{Regularization}} \quad \text{(Eq. 7)}$$

An advantage of this method is that, since only the data consistency term is modified, the same algorithm can be employed to solve the optimization problem (e.g. FISTA, ADMM, DL, etc.).

Similarly, for deep unrolled networks, only the data consistency step $\mathcal{G}$ is modified. The sketched formulations of example equations 5 and 6 are shown in equation 8 and 9, respectively.

$$\mathcal{G}^t(z) = z - \alpha(A_S^t(z - x^t) + A^H(Ax^t - y)) \quad \text{(Eq. 8)}$$

$$\mathcal{G}^t(z) = \operatorname{argmin}_x \frac{1}{2}|A_S^t(x - x^t)|_2^2 + \langle x, A^H(Ax^t - y)\rangle + \frac{\lambda}{2}|x - z|_2^2 \quad \text{(Eq. 9)}$$

Structured Sketching Matrix

We further adapt the IHS formulation to the MR reconstruction problem by providing a structured sketching matrix S denoted eigen-sketching matrix. The structured design of the sketching matrix has three main purposes:

1. Preserve the Fourier structure of the original problem to keep leveraging the high efficiency of the fast Fourier transform.

2. Reduce the number of coils actively used during reconstruction to lower computational burden of the reconstruction procedure.
3. Leverage previous work on coil compression by incorporating the principal component estimation into the sketching matrix.

Figure 1:
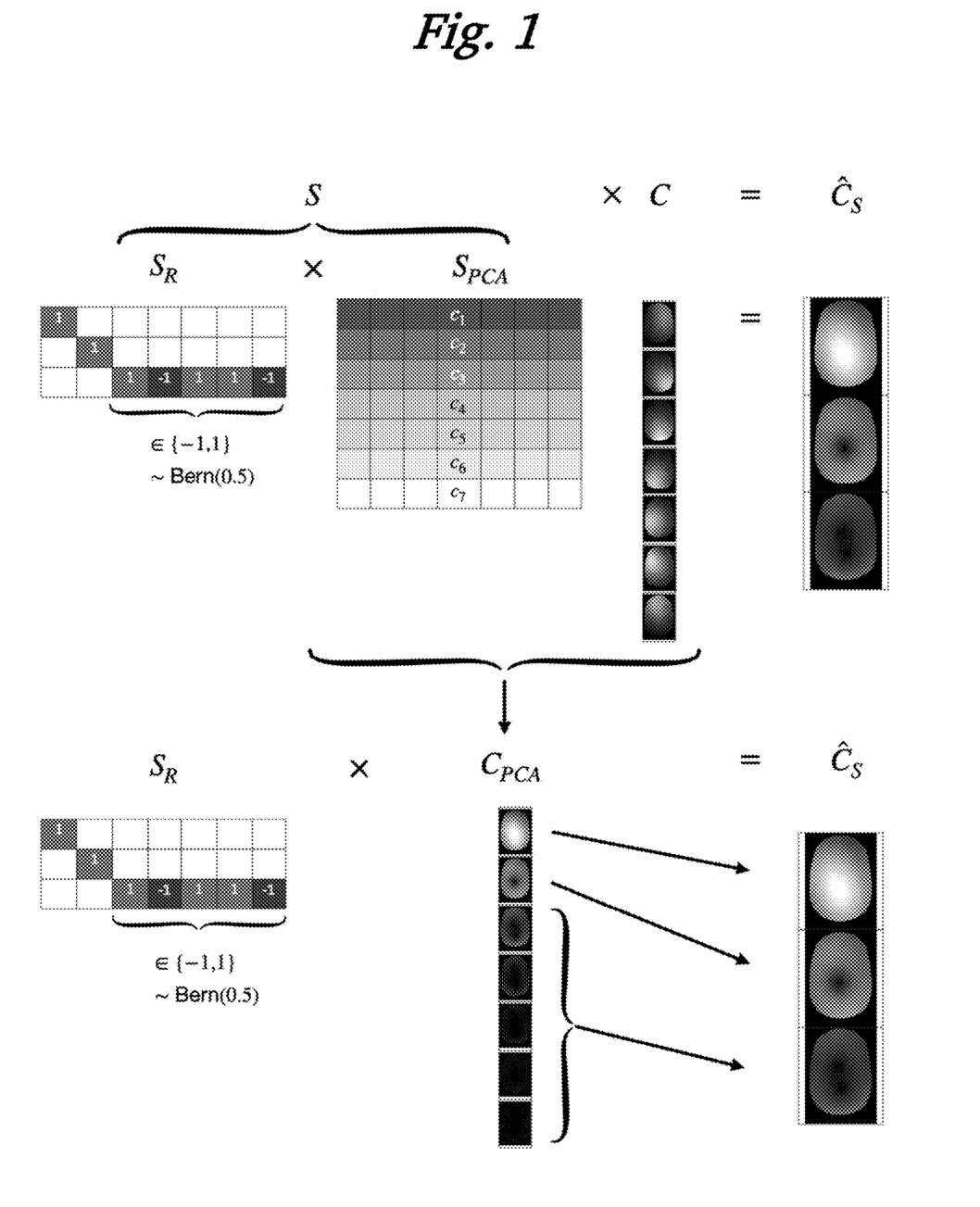
FIG. 1 is a schematic diagram of a structured sketching matrix S illustrating it as the product of two matrices $S_{PCA}$ and $S_R$, and also illustrating a sensitivity map operator $C_{PCA}$ as the product of $S_{PCA}$ by a coil sensitivity map operator C.

FIG. 1 shows the structure of the eigen-sketching matrix, which is composed of two matrices $S_{PCA}$ and $S_R$ that, effectively, combine the data linearly in the coil dimension. The $S_{PCA}$ matrix performs the coil compression transformation [5], which yields a new coil sensitivity map operator $C_{PCA}$ composed by virtual coils sorted in descending energy. Then, $S_R$ proceeds to sketch this new operator. Similarly to coil compression, the $S_R$ matrix considers a reduced number of high-energy virtual coils. But unlike coil compression, the matrix also considers random linear combinations of the remaining low-energy coils. Thus, leveraging data from all the coils. The resulting sketched model matrix $A_S^t$ at iteration t will have the structure showed in Equation 4, where $C_S^t$ represents the sketched sensitivity map operator that performs voxel-wise multiplication by $\hat{c} < c$ coil sensitivity maps.

$$A_S^t = UFC_S^t \qquad \text{(Eq. 10)}$$

Effectively, the computational cost of solving Equation 6 is now linearly proportional to the new number of actively used coils $\hat{c} < c$.

Algorithm Examples

Coil sketching is a general and flexible framework that can be applied to any iterative reconstruction algorithm. Herein, the inventors present the sketched versions of two commonly used reconstruction formulations.

First, the most used formulation: L1-wavelets reconstruction, where the regularization of the reconstruction problems (Eq. 1 and Eq. 7) becomes:

$$R(x) = |\Psi x|_1 \qquad \text{(Eq. 11)}$$

where $\Psi$ is the wavelets transform. Then, the conventional and sketched reconstruction problems can be solved using the ISTA algorithm as described in Algorithm 1 and Algorithm 2, respectively.

| Algorithm 1 Conventional L1-Wavelets reconstruction |
| --- |
| 1:     Initialize $x_0^0$ |
| 2:     for k = 0 to (K − 1) do |
| 3:         $z_{k+1} = x_k^t - \alpha_k A^H (Ax_k - y)$ |
| 4:         $x_{k+1} = \Psi^H \mathcal{T}_\lambda (\Psi z_{k+1})$ |
| 5:     end for |

| Algorithm 2 Sketched L1-Wavelets reconstruction |
| --- |
| 1:     Initialize $x_0^0$ |
| 2:     for t = 0 to (N − 1) do |
| 3:         $g = A^H (Ax_0^t - y)$ |
| 4:         Generate random sketching matrix $S^t$ |
| 5:         $A_S^t = S^t A$ |
| 6:         for k = 0 to (K − 1) do |
| 7:             $z_{k+1}^t = x_k^t - \alpha_{t,k} ((A_S^t)^H A_S^t (x_k^t - x_0^t) + g)$ |
| 8:             $x_{k+1}^t = \Psi^H \mathcal{T}_\lambda (\Psi z_{k+1}^t)$ |
| 9:         end for |
| 10:       $x_0^{t+1} = x_K^t$ |
| 11:     end for | where $\mathcal{J}$ is the soft-thresholding operation with threshold $\lambda$.

Additionally, the inventors present the algorithms for a commonly used DL formulation: MoDL [1], where the data consistency step for the conventional and sketched reconstructions are Eq. 6 and Eq. 9 respectively. The algorithms are presented below:

| Algorithm 3 Conventional MoDL reconstruction |
| --- |
| 1:     Initialize $x_0$ |
| 2:     for k = 0 to (K − 1) do |
| 3:         $z_{k+1} = \mathcal{P}_w(x_k)$ |
| 4:         $x_{k+1} = \arg\min_x \|Ax - y\|_2^2 + \lambda \|x - z_{k+1}\|_2^2$ <br>              $= (A^H A + \lambda I)^{-1} (A^H y + z_{k+1})$ |
| 5:     end for |

| Algorithm 4 Sketched MoDL reconstruction |
| --- |
| 1:     Initialize $x_0^0$ |
| 2:     for k = 0 to (K − 1) do |
| 3:         $z_{k+1} = \mathcal{F}_w(x_k^0)$ |
| 4:         for t = 0 to (T − 1) do |
| 5:             $g = A^H (A z_{k+1}^t - y)$ |
| 6:             Generate random sketching matrix $S^t$ |
| 7:             $A_S^t = S^t A$ |
| 8:             Initialize $x_k^t$ |
| 9:             $x_k^{t+1} = \arg\min_x \frac{1}{2}\|A_S^t(x - x_k^t)\|_2^2 + \langle x, g \rangle + \frac{\lambda}{2}\|x - z_{k+1}\|_2^2$ <br>              $= ((A_S^t)^H A_S^t + \lambda I)^{-1} ((A_S^t)^H A_S^t x_k^t - g + \lambda z_{k+1})$ |
| 10:       end for |
| 11:       $x_{k+1}^0 = x_k^T$ |
| 12:     end for |

Evaluation

First, the inventors tested the method with a non-Cartesian retrospectively undersampled dataset: Abdominal 3D cones acquired with a 20 phases array torso coil. The inventors reconstructed the dataset with L1-wavelets regularization using accelerated versions of Algorithm 1 and Algorithm 2 (FISTA). Then, they compared the convergence of the objective function $f(x)$, memory usage and final image quality of the following three methods:
1. Conventional reconstruction with all c coil.
2. Reconstruction with coil compression using the first coil $\hat{c} < c$ virtual coil.
3. Coil sketching with $\hat{c} < c$ coils.

Second, the inventors tested the feasibility of coil sketching in deep unrolled networks with a Cartesian 3D knee (320 slices) retrospectively undersampled dataset with 8 coil-compressed channels. The datasets were reconstructed using three networks:
1. Baseline network, which accords with the original DL framework.
2. Plug-n-play (PnP) sketched network, which uses the trained baseline network weights, then replaces the data consistency (DC) steps at inference. The aim is to test equivalency of both original and sketched DC steps.
3. Sketched network, network with the sketched data consistency both for training and inference.

Network 1 is described in Algorithm 3, and networks 2 and 3 are described in Algorithm 4. To evaluate training, memory usage and iteration times were compared. To evaluate inference, memory usage, iteration times, and image quality metrics were compared.

Results

Figure 2A:
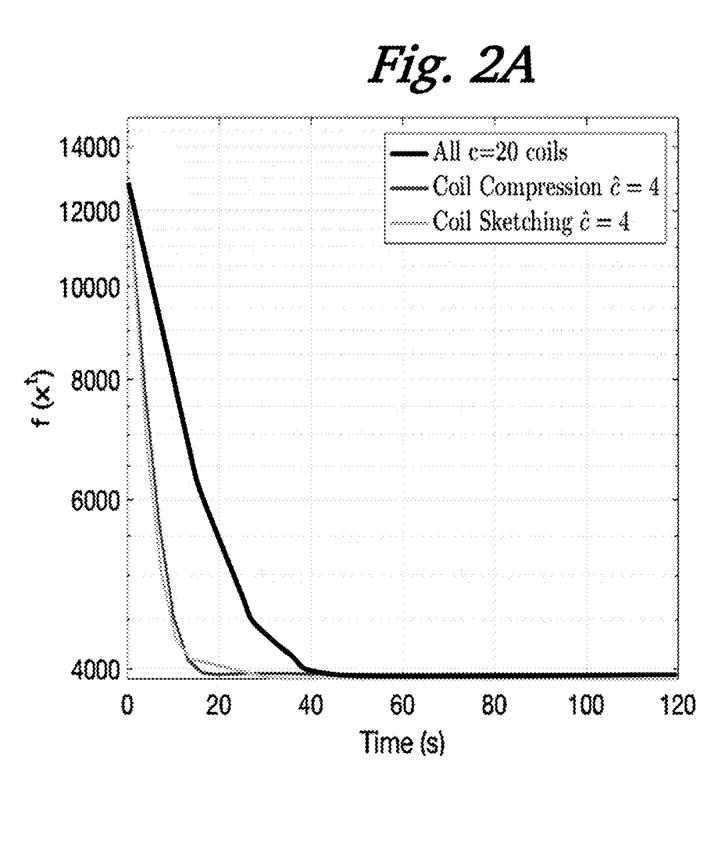
FIGS. 2A-2B are two graphs that show the convergence of the objective functions during reconstruction, of the 3D cones dataset, with conventional reconstruction with all coils, coil compression and coil sketching.
Figure 2B:
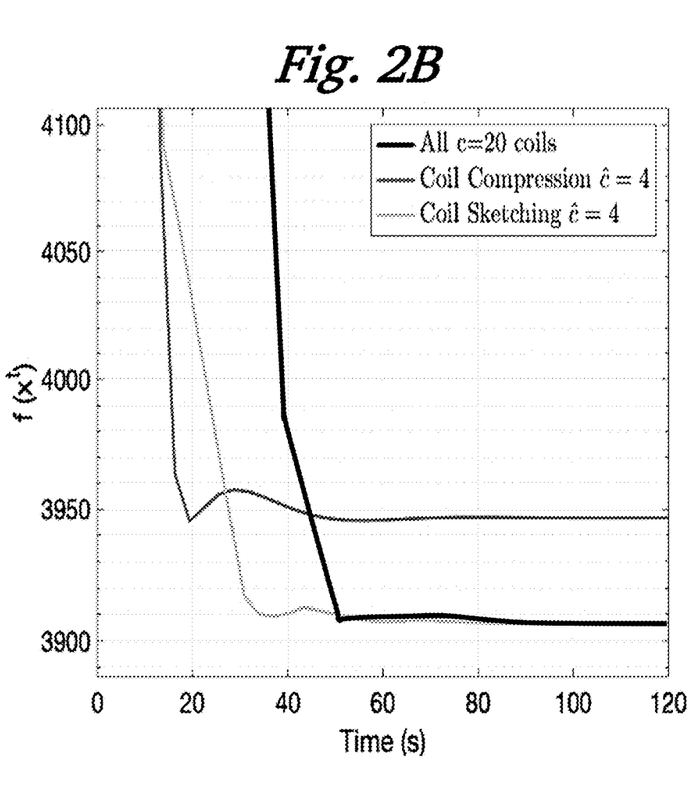
Figure 3:
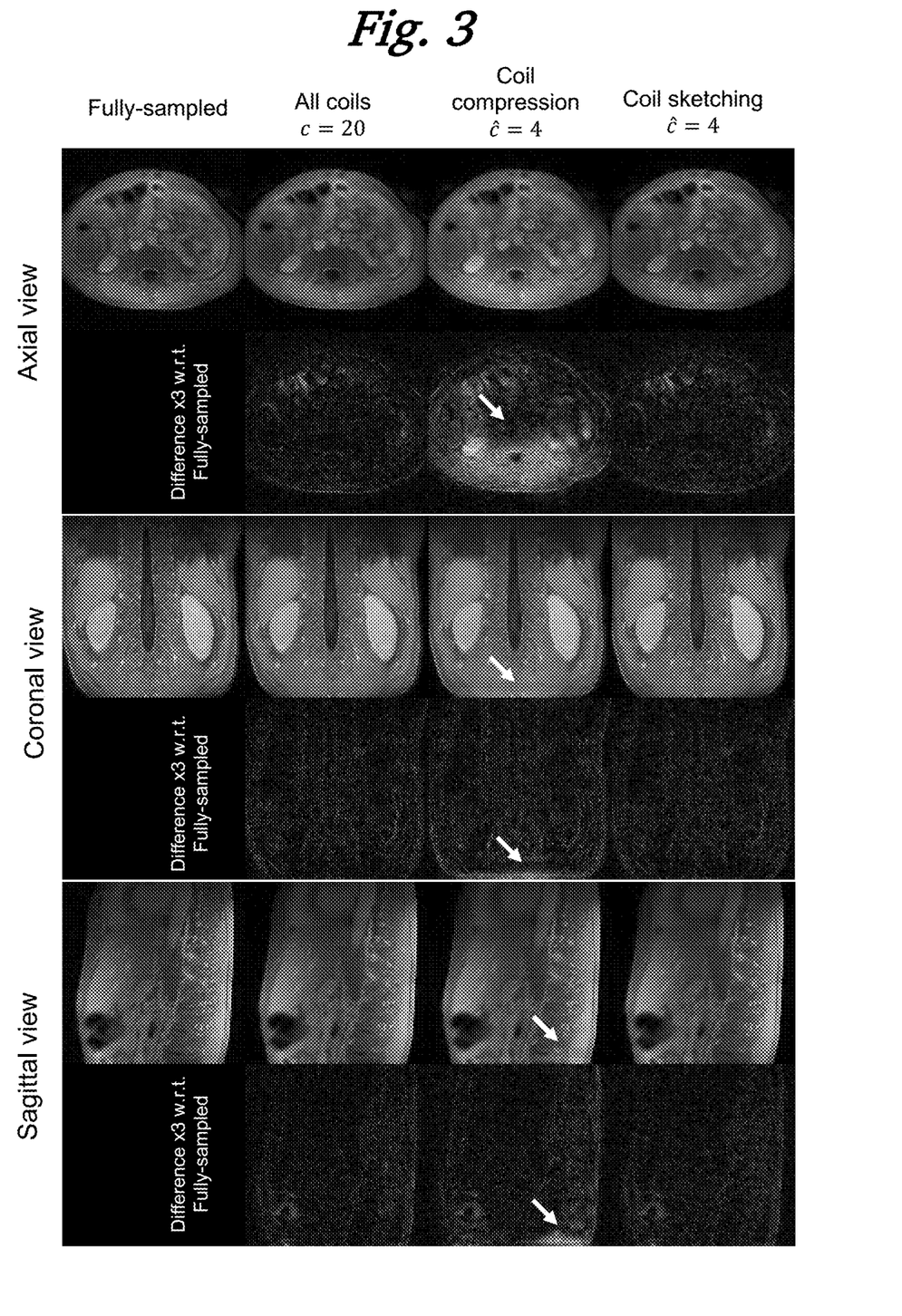
FIG. 3 depicts three grids showing images of reconstruction results for the 3D cones dataset reconstructed with conventional reconstruction with all coils, coil compression and coil sketching.

From the first test with conventional reconstruction, FIGS. 2A-2B show that reconstructions with coil compression and coil sketching run considerably faster than reconstruction using all coils. However, reconstruction with coil compression converges to a suboptimal value, whereas the proposed method attains the optimal value. FIG. 3 shows that this suboptimality is manifested as significant lower image quality and noticeable shading artifacts. Table 1 shows the summarized metrics. Memory usages and reconstruction times are considerably lower for coil compression and coil sketching. However, coil compression presents a significant decrement on image quality metrics, whereas coil sketching yields virtually the same image metrics than conventional reconstruction with all coils.

Figure 4A:
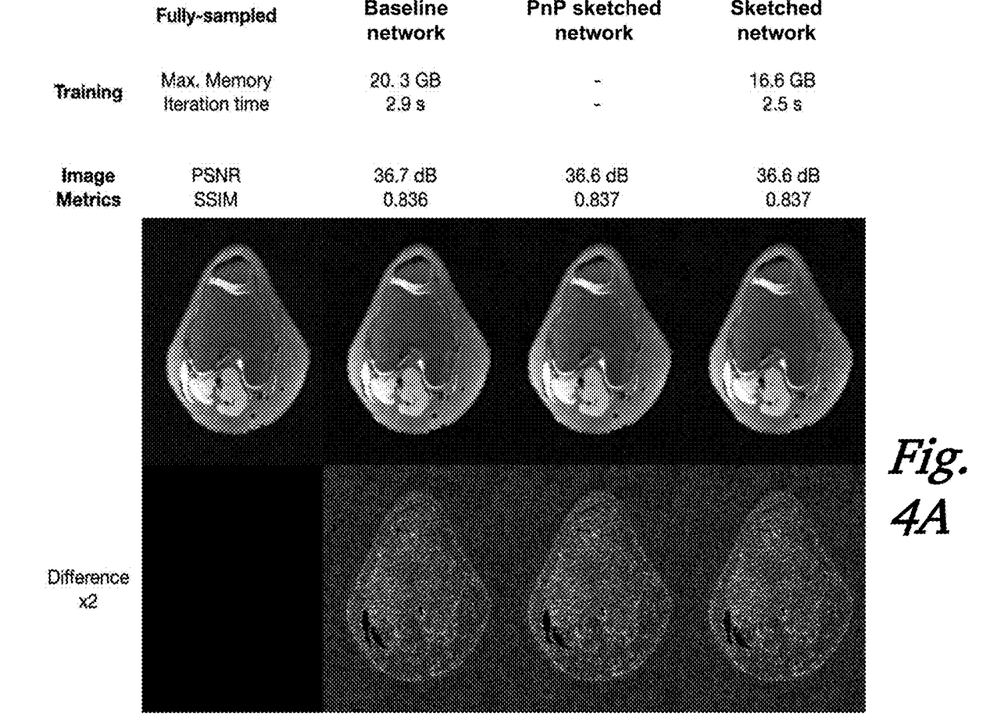
FIGS. 4A-4B are two grids showing images of inference results for two slices from the test dataset reconstructed with baseline MoDL, PnP sketched MoDL, and sketched MoDL.
Figure 4B:
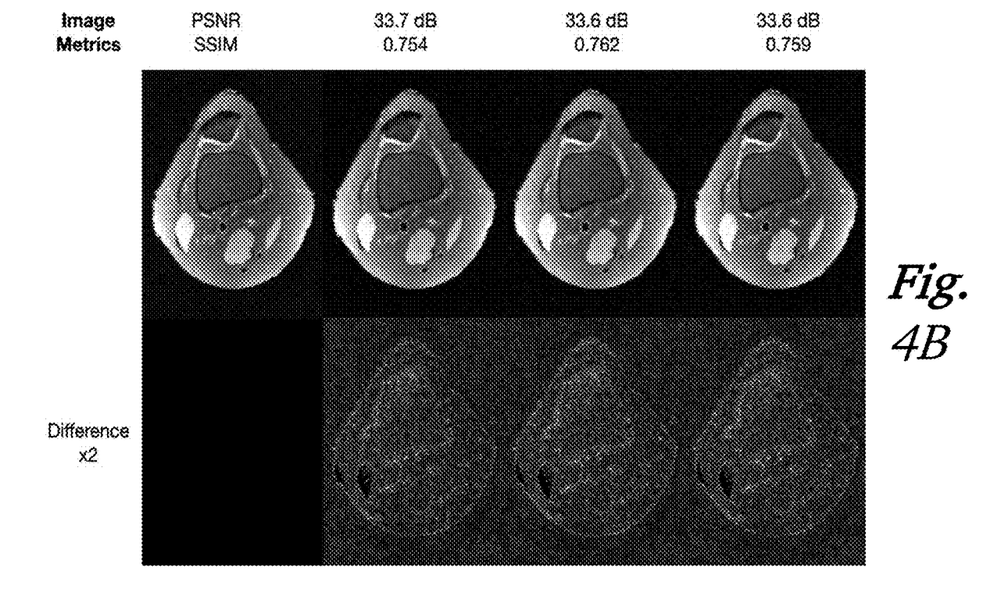

From the second test with DL-based reconstruction, FIGS. 4A-4B show a visual comparison between reconstruction with the three networks discussed above. The graphic presents inference results for two slices from the test dataset reconstructed with the baseline network, the PnP sketched network, and the sketched network shown left-to-right in the four columns. Both visually and through image metrics, the results are marginally different. Table 2 shows the summary of the metrics measured for both training and inference. For training, the sketched network has −18% memory usage and −15% time per iteration. For inference, the three networks have marginally different image metrics.

Discussion

For conventional reconstruction, the inventors tested the method with a non-Cartesian retrospectively undersampled dataset. Reconstructions with coil compression and coil sketching run considerably faster than reconstruction using all coils. However, reconstruction with coil compression converges to a suboptimal value, whereas coil sketching attains the optimal value. This suboptimality is manifested as significant lower image quality and noticeable shading artifacts in the 3D acquisition. Additionally, memory usage of coil compression and coil sketching are considerably lower than conventional reconstruction with all coils. Coil sketching allows faster reconstruction (approximately 2×) and improved memory-efficiency (approximately 5×) with virtually no penalty on reconstruction accuracy, by effectively using fewer coil sensitivity maps and, therefore, fewer Fourier transforms per iteration. This reduced computational cost enables reconstruction of larger datasets with higher resolution and dimensionality.

For DL-based reconstruction, sketched-MoDL shows a promising decrease in training memory usage that could facilitate DL-based reconstruction of higher dimensional datasets, especially for non-cartesian 3D, where efficient coil compression techniques like GCC [6] cannot be used. Additionally, the decrease in iteration time could reduce the total training time by days, since networks are typically trained for tens of thousands of iterations. Additionally, our method can be flexibly integrated into various unrolled methods as a substitute for data-consistency, in contrast to other memory-efficient techniques such as [11] that require invertible layers. Regarding inference, the three networks present virtually the same image metrics, which indicates no penalty on reconstruction accuracy.

TABLE 1

|  | All coils $c = 20$ | Coil compression $\hat{c} = 4$ | Coil Sketching $\hat{c} = 4$ |
|---|---|---|---|
| Max. memory (MB) | 4,719 | 1,070 | 1,150 |
| Recon time (s) | 109 | 57 | 60 |
| PSNR (dB) | 13.6 | 11.9 | 13.7 |
| MS-SSIM | 0.81 | 0.77 | 0.81 |

TABLE 2

|  |  | Baseline network $c = 8$ | PnP network $\hat{c} = 4$ | Sketched network $\hat{c} = 4$ |
|---|---|---|---|---|
| Training | Max. memory (MB) | 20,345 | — | 16,576 (−18%) |
|  | Time per iteration (s) | 2.90 | — | 2.48 (−15%) |
| Inference | SSIM | 0.886 ± 0.002 | 0.889 ± 0.004 | 0.889 ± 0.003 |
|  | PSNR (dB) | 39.94 ± 0.42 | 39.79 ± 0.43 | 39.85 ± 0.42 |
|  | Max. memory (MB) | 1,731 | 2,331 (+35%) | 2,331 (+35%) |
|  | Time per image (s) | 0.51 | 0.39 (−24%) | 0.39 (−24%) |

Conclusion

Herein is disclosed a general and flexible reconstruction algorithm that applies randomized dimension reduction to effectively reduce the computational cost of image reconstruction. The techniques of the invention can be used to reconstruct any undersampled magnetic resonance imaging dataset with increased speed and memory-efficiency. This increased efficiency can be leveraged to afford reconstruction of datasets with higher dimensionality and spatiotemporal resolution. The invention is especially useful for high-dimensional MRI applications that usually have prohibitive computational and memory requirements, e.g., 2D/3D cardiac cine, 3D cones acquisitions, 4D flow, ND flow or dynamic contrast enhanced (DCE) MRI.

Furthermore, deep learning-based reconstruction methods require the use of deep neural networks with millions of parameters, which increases the memory footprint and limits the method to only lower-dimensional MRI techniques such as 2D or 3D acquisitions. The invention can decrease computational cost of training and inference of DL-based reconstruction and could potentially enable applications to higher-dimensional MRI techniques.

In other embodiments, the technique is applied to other types of MR image reconstruction problem formulations besides Eq. 1. For example, it may be applied to low-rank decomposition methods for high-dimensional applications (e.g., 4d flow, ND flow, or DCE). In other embodiments, different structured sketching matrices could be used for $S_R$ and $S_{PCA}$. For $S_R$, other randomized sketching matrices could be tested such as Gaussian sketch or Hadamard sketch. For $S_{PCA}$, other coil compression transformation methods could be used. In other embodiments, other types of iterative sketching algorithms could be used besides Eq. 3, e.g. adaptive sketching methods. In other embodiments, other types of deep unrolled network's data consistency steps ($\mathcal{G}$ operator) could be sketched to improve computational efficiency.

REFERENCES

1. Aggarwal, H. K., Mani, M. P., & Jacob, M. (2018). MoDL: Model-based deep learning architecture for inverse problems. IEEE transactions on medical imaging, 38(2), 394-405.
2. Hammernik, K., Klatzer, T., Kobler, E., Recht, M. P., Sodickson, D. K., Pock, T., & Knoll, F. (2018). Learning a variational network for reconstruction of accelerated MRI data. Magnetic resonance in medicine, 79(6), 3055-3071
3. Sandino, C. M., Cheng, J. Y., Chen, F., Mardani, M., Pauly, J. M., & Vasanawala, S. S. (2020). Compressed sensing: From research to clinical practice with deep neural networks: Shortening scan times for magnetic resonance imaging. IEEE signal processing magazine, 37(1), 117-127.
4. Yang, Y., Sun, J., Li, H., & Xu, Z. (2018). ADMM-CSNet: A deep learning approach for image compressive sensing. IEEE transactions on pattern analysis and machine intelligence, 42(3), 521-538.
5. Huang, F., Vijayakumar S., Li, Y., Hertel, S., & Duensing, G. R., (2008). A software channel compression technique for faster reconstruction with many channels," Magnetic resonance imaging, vol. 26, no. 1, pp. 133-141.
6. Zhang, T., Pauly, J. M., Vasanawala, S. S., & Lustig, M. (2013). Coil compression for accelerated imaging with Cartesian sampling. Magnetic resonance in medicine, 69(2), 571-582.
7. Oscanoa, J. A., Ong, F., Li, Z., Sandino, C. M., Ennis, D. B., Pilanci, M., & Vasanawala, S. S. Coil Sketching for fast and memory-efficient iterative reconstruction. ISMRM 28$^{th}$ Annual Meeting, May 15-20$^{th}$ 2021 (Virtual meeting).
8. Oscanoa J A, Ozturkler B, Iyer S S, Li Z, Sandino C M, Pilanci M, Ennis D B, Vasanawala S S. Coil-sketched unrolled networks for computationally-efficient deep MRI reconstruction. ISMRM 30th Annual Meeting, London, United Kingdom, May 6-12$^{th}$ 2022
9. Pilanci, M., & Wainwright, M. J. (2016). Iterative Hessian sketch: Fast and accurate solution approximation for constrained least-squares. The Journal of Machine Learning Research, 17(1), 1842-1879
10. Pilanci, M., & Wainwright, M. J. (2015). Randomized sketches of convex programs with sharp guarantees. IEEE Transactions on Information Theory, 61(9), 5096-5115
11. Kellman M., Zhang K., Markley E., Tamir J., Bostan E., Lustig M., and Waller L., (2020). Memory-efficient learning for large-scale computational imaging," IEEE Transactions on Computational Imaging, vol. 6, pp. 1403-1414.

The invention claimed is:

1. A method for magnetic resonance imaging comprising:
acquiring with multiple receiver coils of an MRI imaging apparatus pseudorandomly undersampled k-space imaging data;
performing MR image reconstruction to produce a reconstructed MR image from the pseudorandomly undersampled k-space imaging data;
wherein the reconstruction comprises iteratively solving sketched approximations of an original reconstruction problem, wherein the sketched approximations use a sketched model matrix $A_s$ that is a lower-dimensional version of an original model matrix A of the original reconstruction problem;
wherein the sketched model matrix $A_s$ preserves the Fourier structure of the MR reconstruction problem and reduces the number of coils actively used during reconstruction.

2. The method of claim 1 wherein the pseudorandomly undersampled k-space imaging data have both spatial and temporal dimensions.

3. The method of claim 1 wherein iteratively solving the sketched approximations of the original reconstruction problem comprises iteratively solving second-order Taylor approximations with a sketched Hessian that includes the sketched model matrix $A_s$.

4. The method of claim 1 wherein the sketched model matrix $A_s$ is related to the original model matrix A by $A^t_s = S^t A$, where S is a structured sketching matrix.

5. The method of claim 4 wherein the structured sketching matrix S is the product of two matrices $S_{PCA}$ and $S_R$, where $S_{PCA}$ estimates virtual coils from principal components and $S_R$ sketches the virtual coils.

6. The method of claim 5 wherein $S_R$ sketches a reduced number of high-energy virtual coils and also includes random linear combinations of remaining low-energy coils.

7. The method of claim 5 wherein multiplication of $S_{PCA}$ by a coil sensitivity map operator C produces a sensitivity map operator $C_{PCA}$ with virtual coils sorted according to descending energy.

* * * * *